United States Patent [19]
Stimpson

[11] Patent Number: 5,387,790
[45] Date of Patent: Feb. 7, 1995

[54] LIGHT INTENSITY DETECTION AND MEASUREMENT CIRCUIT FOR MEASURING THE DURATION OF THE DISCHARGE CYCLE OF A CAPACITOR NETWORK

[75] Inventor: Donald I. Stimpson, Gurnee, Ill.

[73] Assignee: Abbott Laboratories, Abbott Park, Ill.

[21] Appl. No.: 127,470

[22] Filed: Sep. 27, 1993

[51] Int. Cl.⁶ .............................................. H01J 40/14
[52] U.S. Cl. ................................ 250/214 RC; 327/514
[58] Field of Search .................. 250/214 RC, 214 LS, 250/214 SW, 214 A, 214 PR, 214.1; 377/20, 12, 95, 53, 58; 307/311

[56] References Cited

U.S. PATENT DOCUMENTS

| | | | |
|---|---|---|---|
| 3,748,044 | 7/1973 | Liston | 356/180 |
| 4,614,866 | 9/1986 | Liss et al. | 250/214 RC |
| 4,786,797 | 11/1988 | Ely | 250/214 R |

Primary Examiner—David C. Nelms
Assistant Examiner—Que T. Le
Attorney, Agent, or Firm—Richard D. Schmidt; Mark C. Bach

[57] ABSTRACT

A circuit measures the intensity of a monitored light beam by generating a signal which is of a specific time duration corresponding to light intensity. The circuit utilizes a photosensitive element for receiving the light and producing a variable control signal in direct correspondence to the light intensity. A capacitor network is placed in series with the photosensitive element, wherein the time duration for discharging the capacitor network is directly correlated to the intensity of the collected light.

18 Claims, 3 Drawing Sheets

LIGHT INTENSITY DETECTION AND MEASUREMENT CIRCUIT FOR MEASURING THE DURATION OF THE DISCHARGE CYCLE OF A CAPACITOR NETWORK

BACKGROUND OF INVENTION

1. Field of Invention

The invention is generally related to apparatus for measuring the intensity of a light beam and is specifically directed to a circuit for measuring the intensity of light by correlating light intensity to a time signal.

2. Description of the Prior Art

There are numerous applications where the intensity of a light beam passing through a medium is indicative of conditions existing in the medium. For example, Abbott Laboratories, the assignee of the subject application, has developed a number of chromatographic immunoassay analyzers for the determination of certain conditions existing in organic samples. The assay typically utilizes a single disposable housing with a strip of laminated nitrocellulose or the like attached to a glass fiber pad. The assay is exposed to a reference light source which is passed through the medium, The emitted light is collected at a sampler for measuring its intensity. The intensity of the light is indicative of the conditions of the sample. This type of measurement has been particularly useful in screening and providing a qualitative human chorionic test for prompt detection of pregnancy and evaluation of problem pregnancies.

Light intensity detection circuits for use with these types of analysis schemes are relatively well known. Typically the light intensity is detected by using a photosensitive element which is capable of generating a voltage signal which is then amplified and converted to a digital signal by an analog-to-digital (A/D) converter. The A/D converter generates a variable level signal for introduction into a microprocessor, wherein the signal level is compared to a reference signal in order to correlate the collected signal with a predetermined reference to "read" the sample.

Examples of A/D converters are shown and described in U.S. Pat. No. 4,779,074, entitled: *Low Level Voltage Pulse Converter*, issued to R. E. Whitford, :et al. on Oct. 18, 1988, and U.S. Pat. No. 4,178,585, entitled: *Analog to Digital Converter*, issued to K. Takagi, et al. on Dec. 11, 1979.

The known devices for utilizing light intensity sampling in order to determine conditions of a sample universally use A/D converters along the lines described in the above patents to determine the intensity of the light by producing a converted digital signal of varying levels, corresponding to measured light intensity. For example, European Patent Application No. 0479394A3 by R. Phillipps, et al., filed on Aug. 7, 1987, discloses a method and apparatus for determination of analytes. A light source is directed toward a sample and a detector collects the emitted light. The intensity level of emitted light is utilized to determine the condition of the sample. As shown in that application, the emitted light is converted into an analog signal which is then amplified and converted into a digital signal through an A/D converter, with the digital output of the converter being introduced into the microprocessor. U.S. Pat. No. 4,766,083 entitled: *Method for the Photometric Determination of Biological Agglutination*, issued to M. Yoshinobu, et al. on Aug. 23, 1988, discloses a photometric method and apparatus for measuring agglutination in a biological agglutination reaction system test sample using a laser beam source and a photodetector for detecting light scattered by the test sample. The light collected by the photosensitive element is converted from an analog signal to a digital signal before processing.

While these devices provide accurate sampling techniques, and the analog to digital conversion scheme is suitable for accomplishing the desired result, there remain disadvantages to the use of A/D converters in light intensity analysis systems. Primarily, the cost associated with high resolution A/D chips has prohibited the widespread adoption of light spectrum analysis systems. A typical analog to digital converter network having a 16 bit converter capability can cost several hundred dollars. Where 24 bit resolution is required, the cost can increase by dramatic proportions. Thus, one of the most expensive, prohibitive components in the system is the converter network. Therefore, if the cost of the signal conversion can be greatly reduced, the applicability of light spectrum analysis equipment can be greatly enhanced at reduced cost, providing better testing capability for broader based sampling systems.

At present, there remains a need to develop a system permitting the application of light intensity detection systems utilizing conversion equipment in an efficient yet accurate effective manner.

SUMMARY OF THE INVENTION

The subject invention provides an improved system for measuring light intensity utilizing photosensitive elements without requiring the use of an A/D converter. In the preferred embodiment, the A/D converter is replaced by a timer which is readily implemented in a microprocessor controlled device. The light intensity detection circuit includes a photosensitive element which is positioned to receive the light emitted from a sample which is in position to receive the source light beam. The photosensitive element operates in typical manner to develop a variable resistance level in direct correspondence to the intensity of the emitted light beam. A capacitor network is positioned in series with the photosensitive element and a power source is coupled to the capacitor network and the photosensitive element for charging the capacitor network through the variable resistance of the photosensitive element. The duration of the discharge cycle of the capacitor network is controlled by and is in direct correlation with the variable resistance level of the photosensitive element, as determined by the collected light.

In typical operation, as the intensity of the light increases, the resistance of the photosensitive element is reduced, permitting the capacitor network to discharge more quickly. Thus, a direct correspondence to light intensity can be measured by the duration of the discharge cycle of the capacitor network.

The photosensitive element of the preferred embodiment defines a control element adapted for receiving light emitted from the light source for producing a variable control parameter corresponding to the intensity of the collected light. By combining a timer network with the control element, responsive to the variable control parameter, the timer can be utilized to determine the light intensity. The timer signal is introduced into a microprocessor system in the manner well known, by which the signal can be compared to reference parameters in order to determine the condition of the sample being analyzed.

By utilizing the light intensity detection circuit of the present invention, a cost savings of over 400% can be achieved when compared to a system utilizing a typical 16 bit analog to digital converter network. For example, at the present time, a 16 bit analog digital converter chip can cost as much as $20.00. This can be replaced with an operational amp and an Intel 87C51 microprocessor operating at 12 megahertz for the timing function to achieve an equivalent to 17 bit resolution, for a cost of approximately $1.00.

Thus, the subject invention provides a low cost, accurate detection circuit for measuring the intensity of a collected light beam. The invention makes possible a wide spread application of light detection sampling techniques in fields where such equipment has not been available because cost is prohibitive.

Therefore, it is an object and feature of the invention to provide a low cost, accurate light detection circuit for use in determining the intensity of a collected light beam.

It is another object and feature of the invention to provide an improved light intensity detection circuit utilizing a photosensitive element in combination with a capacitor network to provide an accurate correlation of collected light intensity with a time measured signal.

It is yet another object and feature of the subject invention to provide a timing network for correlating the intensity of a light signal to a time measurement utilizing a control element for receiving the light and a timer network and producing a variable control parameter corresponding to the intensity to the light and a timer network responsive to the variable control parameter for producing a time signal.

Other objects and features of the invention will be readily apparent from the accompanying drawings and detailed description of the preferred embodiments.

BRIEF DESCRIPTIONS OF THE DRAWINGS

DETAILED DESCRIPTION OF THE PREFERRED EMBODIMENT

Figure 1:
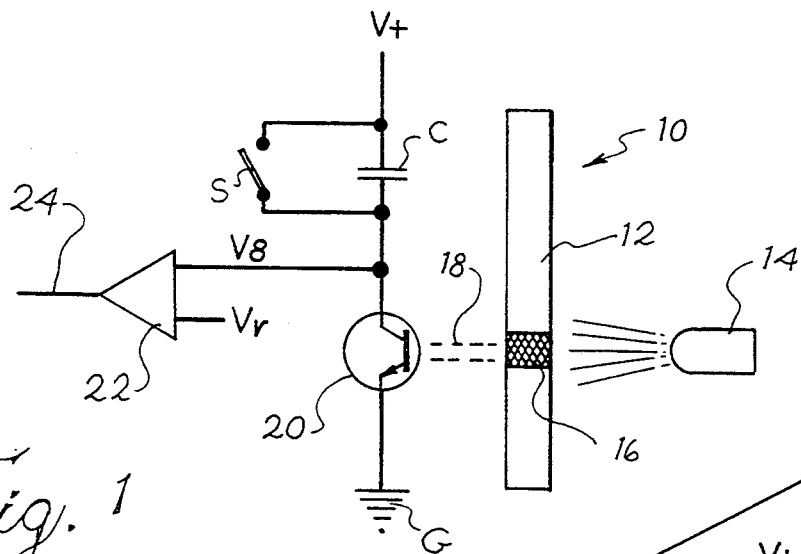
FIG. 1 is a basic circuit diagram illustrating the features of the subject invention.

As shown in FIG. 1, a typical analytical device for an analyte or sample to be analyzed utilizing light intensity is designated by the reference numeral 10 and includes a carder or assay devise 12, which can be a chromatographic material, at least a portion of which is adapted for transmitting light from a reference source such as the LED 14. The sample or assay reaction product 16 is positioned at a predetermined situs to receive the light emitted from the source 14.

An example of an assay device which could be utilized in the practice of the present invention include "dipstick" and "flow-through" devices and methods and may comprise a chromatographic material, or carrier, having a proximal end and a distal end, wherein the test sample can travel from the proximal end to the distal end by capillary action. The chromatographic material, usually, contains a capture reagent, immobilized in a capture situs, that is capable of binding to a member selected from the group consisting of the analyte, an ancillary specific binding member, an indicator reagent and combinations thereof. An application pad may be in fluid flow contact with the proximal end of the chromotographic material, in this instance, the application pad receives the test sample and may contain a diffusive indicator reagent capable of migrating from the application pad to the chromatographic material. An indicator reagent is usually capable of binding to a member selected from the group consisting of the analyte, an ancillary specific binding member, the capture reagent and combinations thereof. The capture and retention of the assay reaction product, which may include an indicator reagent at the predetermined capture situs, results in a detectable response when the device is interposed between the source 14 and the photosensitive element on phototransistor 20. Those skilled in the art will recognize that a method for performing an assay, utilizing such "flow-through" type devices comprises the steps of: applying the test sample to the test device; and reading the results at the capture situs. Once the sample has been applyed to the device, the device may then be interposed in the light intensity detection circuit of the present invention and the presence or amount of a detectable response can be corolated, in a known manner, to the presence or amount of analyte in the test sample. The condition of the sample or reaction product impacts the intensity of the light passing therethrough, and the emitted light, as indicated at 18 is adapted to be received by a control element such as the photosensitive element or phototransistor 20.

In typical manner, the phototransistor 20 develops a variable resistance dependent upon the intensity of the light of the emitted beam 18. Typically, as the emitted beam 18 increases in intensity, the resistance of the phototransistor 20 decreases.

The phototransistor 20 is pan of an electrical circuit having a source voltage as indicated by the voltage source V+. In typical operation, the voltage source is a low voltage (5 vdc) power supply. A capacitor C is positioned in series in the network comprising the voltage source, the capacitor, and the phototransistor. In the preferred embodiment, a switching network S is coupled in parallel across the capacitor and can be used to by pass the capacitor.

In operation, the capacitor C is initially charged. The emitted light beam 18 is then collected on the phototransistor 20, to control the resistance therethrough. The switch S is then opened, allowing the capacitor to discharge through the phototransistor. The capacitor will discharge over a time cycled duration, in accordance with the inverse product of the capacitance and the resistance generated by the phototransistor, or: 1/RC in the well known manner.

In the preferred embodiment, the voltage signal present during the charge up cycle is measured and picked off of the circuit as indicated by $V_s$. This is introduced into an operational amplifier 22 along with a reference signal $V_r$. The combined signal is introduced to a microprocessor or other computer driven system, as indicated at 24.

In the preferred embodiment, the time-to-charge (TTC) the capacitor C is equal to the inverse of the product of the resistance R and the capacitance C multiplied by the natural log of the signal $V_r$ over the source voltage V+, or:

$$TTC = -RCln\frac{Vr}{Vt}$$

Figure 2:
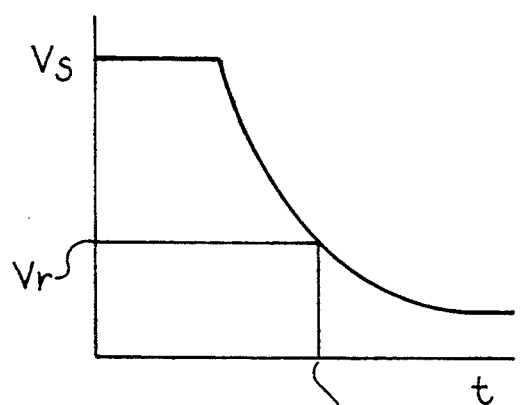
FIG. 2 is a graph showing the correlation of the charge network and time duration signal to the intensity of the collected light beam.
Figure 4:
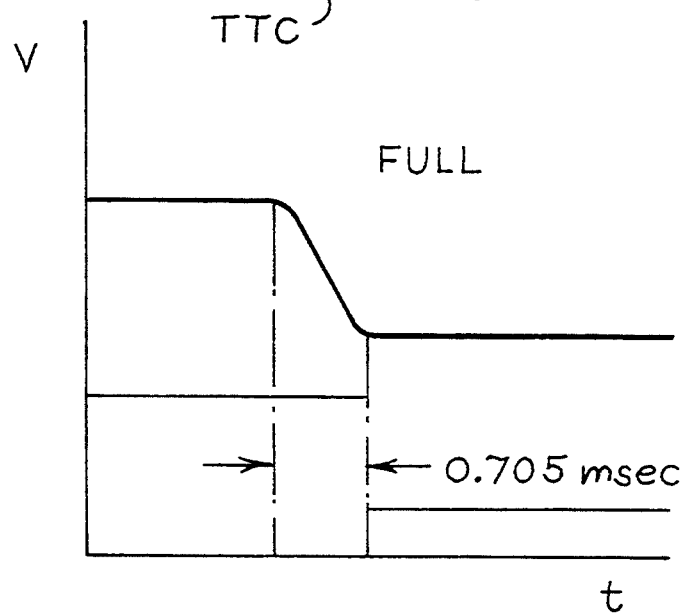
FIGS. 4–8 are graphs illustrating the correlation of light intensity to the time duration signa using the preferred embodiment.
Figure 5:
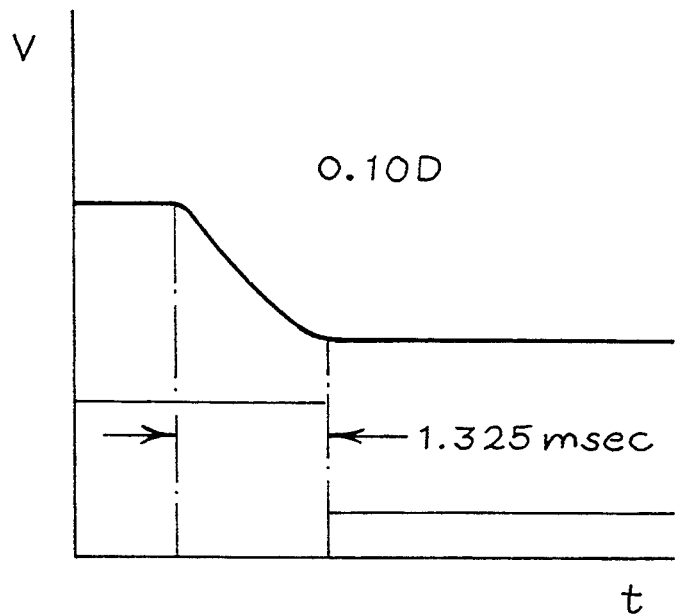
Figure 6:
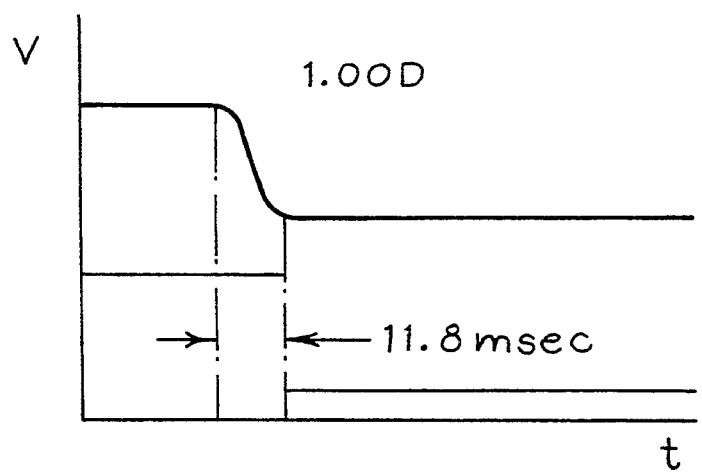
Figure 7:
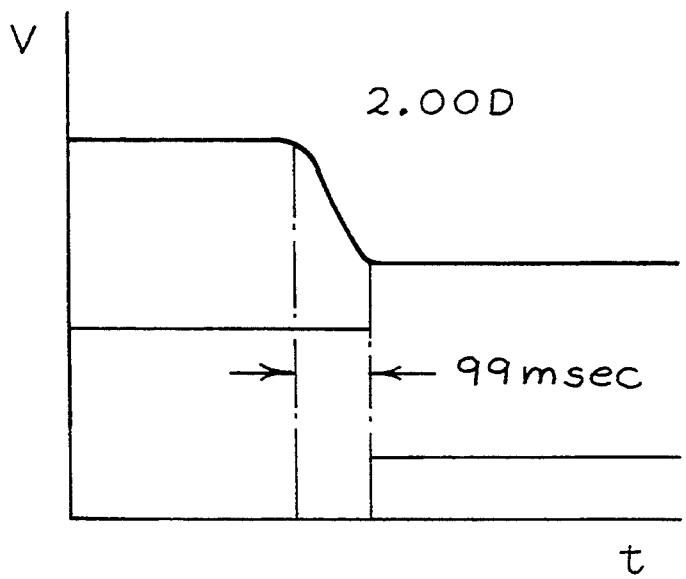
Figure 8:
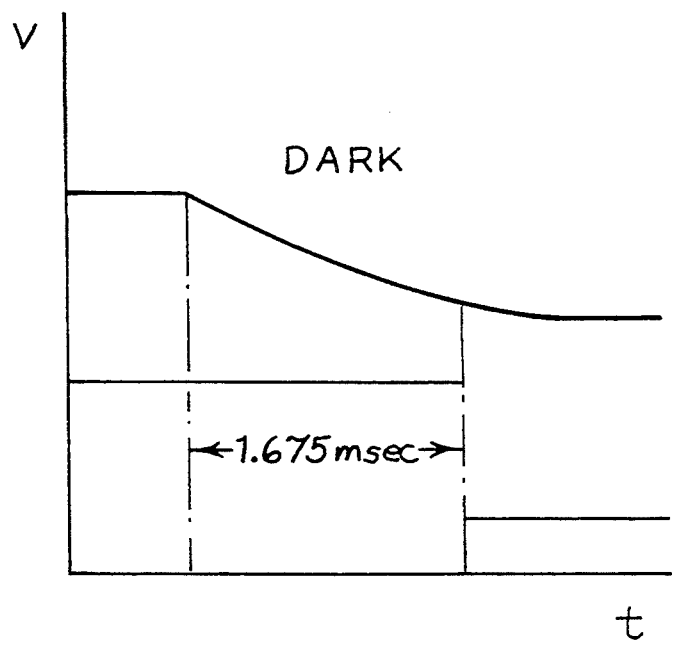

By monitoring the time-to-charge (TTC), the intensity of the light can be determined. A graph illustrating this is shown in FIG. 2. As there shown, the time duration signal $V_s$ is measured along the vertical axis and the time-to-charge (TTC) is measured along the horizontal axis, where:

$$V_s = V + (e^{-t}/RC).$$

Figure 3:
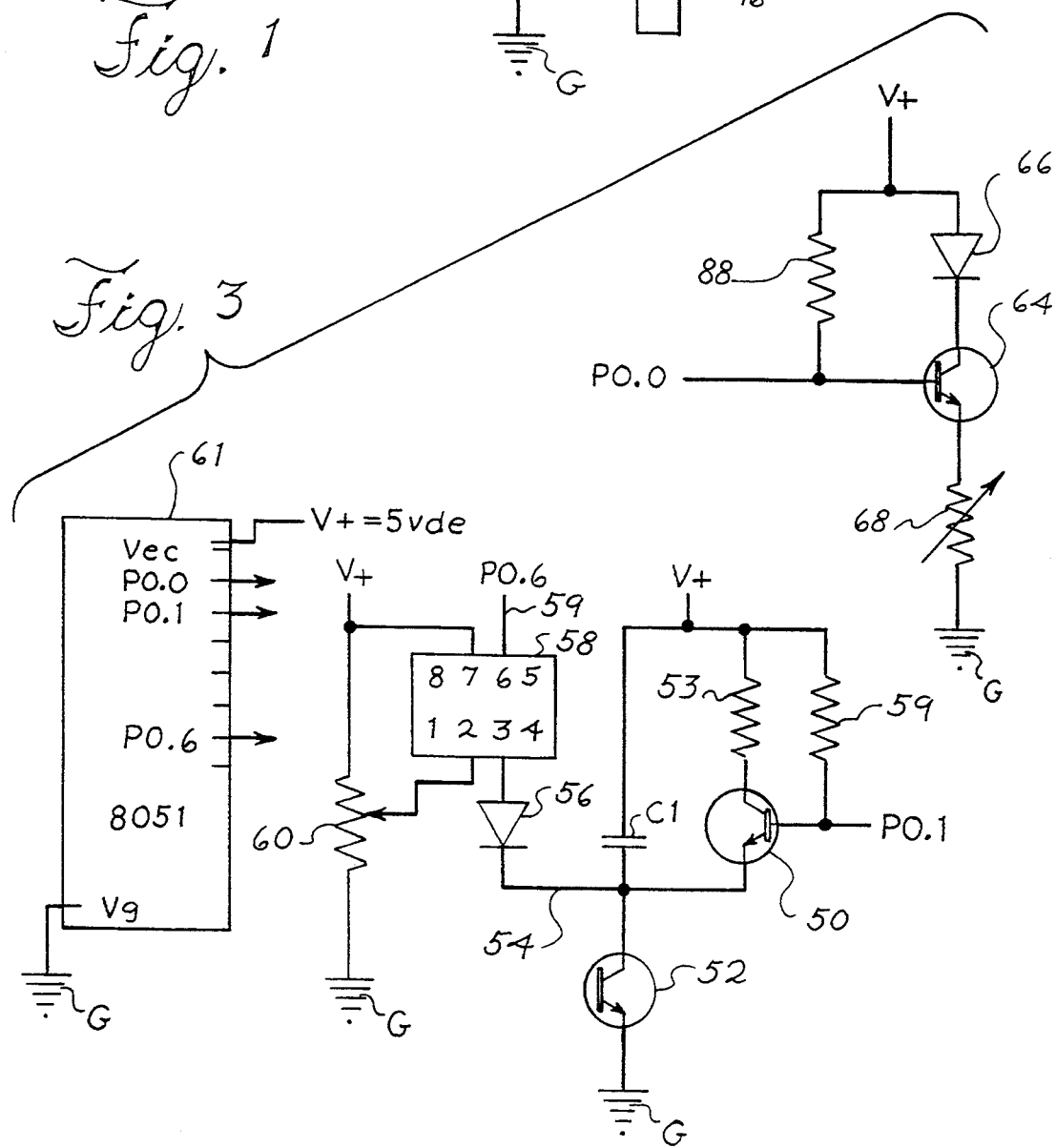
FIG. 3 is a detailed circuit diagram illustrating the preferred embodiment of the subject invention.

A detailed circuit for operating for the subject invention is more clearly shown in FIG. 3, wherein the control element 50 (in the preferred embodiment, a Motorola MRD711 phototransistor) 52 is combined in a network with the capacitor C1 and the voltage source V+. The pn2222A transistor 50 provides the switching network and is connected across the capacitor C1 through a 4.7K ohm resistor 53 and a 33K ohm bypass resistor 59 for controlling the 0.01 microfarad capacitor C1. The 0.01 microfarad capacitor C1 is in series with the photoresistor 52 which is coupled to ground G, for completing the circuit between the voltage source V+, the capacitor and the phototransistor. The time duration signal Vs is picked between the capacitor C1 and the phototransitor 52, on line 54.

In the preferred embodiment, an IN914 blocking diode 56 is placed in the circuit in advance of the operational amplifier/comparator circuit 58. The operational amplifier is a Motorola LN308A9 amplifier, and the pin numbers shown are those of the manufacturer. The signal on line 54 from the sampling circuit is introduced on pin 3. A reference voltage or signal is introduced on pin 2, as shown and is produced by providing a power supply, which is the direct voltage source V+, in combination with a potentiometer 60, or other variable signal generator. The output of the comparator 58 is produced on pin 6 and is introduced via line 59 to pin 6 of the Intel 8051 microprocessor.

An example for establishing the feasibility and operability of the invention was set up utilizing the LED circuit also shown in FIG. 3. A power signal was picked off of pin 0 of the Intel 8051 microprocessor and introduced via line 62 to an LED 66. In the example, the LED utilized was a Ledtronics L200CW65H green LED. The LED 64 was coupled across the power supply V+ in typical fashion with an PN2222 transistor switch 64 in advance of the LED 66 and a variable 1K ohm potentiometer 68 in series to vary the intensity of the signal through the LED for varying light intensity. As is typical, a 33K ohm resistor 88 is looped between the transistor 64 and the control power line 62.

In the test sample, the green LED was varied from OFF (or dark current) to FULL LIGHT in increments, with the charge of the time-to-charge (TTC) for the capacitor, C1 as follows:

| Light Intensity | Time in Milliseconds |
| --- | --- |
| Full Light | 0.705 |
| 0.10 OD | 1.0325 |
| 1.00 OD | 11.8 |
| 2.00 OD | 99.0 |

| Light Intensity | Time in Milliseconds |
| --- | --- |
| Dark Current | 1675.0 |

Graphs illustrating the intensity (or optical density) versus time duration for each of the samples are shown in FIGS. 4-8. The upper trace of the graph is the voltage on the capacitor and the lower trace is the output from the operational amplifier/comparator. As can be seen from the graphs, there is a direct, in fact linear, correlation between the discharge rate of the capacitor and the time duration of the signal, indicating with high accuracy the intensity of the light beam.

The subject invention has been found to be particularly useful for providing a low cost, accurate mechanism for measuring the intensity of a light beam collected at a control element. By correlating the intensity light beam to a time duration signal, the intensity can be determined by measuring time duration, reducing the need to provide an expensive analog-to-digital converter.

While certain features and embodiments of the invention have been described in detail herein, it will be readily understood that the invention encompasses all of the modifications and enhancements within the scope and spirit of the following claims.

What is claimed is:

1. A light intensity detection circuit for determining the intensity of a light source, comprising:
   a. a photosensitive element positioned to receive the light emitted from the light source, said photosensitive element developing a variable resistance level in direct correspondence to the intensity of the light;
   b. a capacitor network in series with the photosensitive element;
   c. a power source coupled to the capacitor network and the photosensitive element and adapted for charging the capacitor network; and
   d. means for measuring the duration of the discharge cycle of the capacitor network through the resistance developed by the photosensitive element in response to the intensity of the light emitted by the light source, wherein the light intensity is related to the duration of the discharge cycle.

2. The light intensity detection circuit of claim 1, further including a switching element for selectively activating and deactivating the capacitor network.

3. The light intensity detection circuit of claim 1, wherein the photosensitive element is a phototransistor.

4. The light intensity detection circuit of claim 2, wherein the switching element is a transistor switch adapted for discharging the capacitor network when the transistor is in the ON condition.

5. The light intensity detection circuit of claim 1, wherein the switching element is in parallel with the capacitor network.

6. The light intensity detection circuit of claim 1, wherein the means for measuring the duration of the discharge cycle comprises a comparator having a reference level signal against which the measured signal is compared for determining the intensity of the emitted light relative to a reference point.

7. The light intensity detection circuit of claim 6, wherein the reference level signal is provided by a reference level signal generator comprising a power source and a variable signal generator.

8. The light intensity detection circuit of claim 6, wherein the comparator further comprises an operational amplifier.

9. The light intensity detection circuit of claim 1, wherein the light intensity is directly proportional to the duration of the charge cycle of the capacitor network.

10. The light intensity detection circuit of claim 6, wherein the duration of the charge cycle is the inverse of the product of the resistance and the capacitance multiplied by the natural logarithm of the reference signal divided by the source.

11. The light intensity detection circuit of claim 10, wherein the measured signal is the source multiplied by "e" to the negative power of the derivative of the inverse product of the resistance and the capacitance.

12. A timing network for correlating the intensity of a light signal to a time measurement, comprising:
 a. an control element adapted for receiving light emitted from a light source and adapted for producing a variable control parameter in a relationship corresponding to the intensity of the emitted light;
 b. a timer network responsive to the variable control parameter and adapted for producing a signal of a time duration relating to the control parameter; and
 c. a power source for driving the control element and the timer network.

13. The timing network of claim 12, wherein the control element, the timer network, and the power source are in series.

14. The timing network of claim 12, wherein the control element comprises a photosensitive element positioned to receive the light emitted from the light source, said photosensitive element developing a variable resistance level in direct correspondence to the intensity of the light.

15. The timing network of claim 14, wherein the timer network comprises a capacitor network in series with the photosensitive element, and wherein there is further included means for measuring the duration of the charge cycle of the capacitor network through the resistance developed by the photosensitive element in response to the intensity of the light emitted by the light source, wherein the light intensity is directly related to the duration of the charge cycle.

16. The timing network of claim 12, wherein the light intensity is directly proportional to the duration of the charge cycle of the capacitor network.

17. A method for detecting the presence or amount of an analyte in a sample comprising:
 providing a test device comprising a chromatograph, i.e. material having a proximal end and a distal end, wherein a test sample can travel from said proximal end to said distal end by capillary action, an analyte capture reagent immobilized in a capture situs on in said chromatographic material, wherein said capture reagent is capable of binding to a member selected from the group consisting of the analyte, an ancillary specific binding member, an indicator reagent and combinations thereof, said test device further comprising a sample receiving situs on said chromatographic material proximal end a diffusive indicator reagent capable of migrating with said sample along said chromatographic material and capable of binding to a member selected from the group consisting of the analyte, an ancillary specific binding member and said capture reagent, wherein the binding of said indicator reagent provides a detectable response at said capture situs thereby indicating the presence or amount of the analyte in the test sample;
 applying a sample to said test device;
 providing a light source and a light intensity detection circuit comprising;
  a. a photosensitive element positioned to receive the light emitted from the light source, said photosensitive element developing a variable resistance level in direct correspondence to the intensity of the light;
  b. a capacitor network in series with the photosensitive element;
  c. a power source coupled to the capacitor network and the photosensitive element and adapted for charging the capacitor network; and
  d. means for measuring the duration of the discharge cycle of the capacitor network through the resistance developed by the photosensitive element in response to the intensity of the light emitted by the light source, wherein the light intensity is related to the duration of the discharge cycle;
 detecting the presence or amount of said detectable signal at the test device capture situs by interposing said test devise between said light source and said light detecting circuit; and correlating the presence at amount of said detectable respond to the presence or amount of said analyte in said sample.

18. A method for detecting the presence or amount of an analyte in a sample comprising providing a flow-through or dipstick type test device comprising a predetermined capture situs on a chromatographic medium applying a test sample to said test device;
 providing a light source and a light intensity detection circuit comprising;
  a. a photosensitive element positioned to receive the light emitted from the light source, said photosensitive element developing a variable resistance level in direct correspondence to the intensity of the light;
  b. a capacitor network in series with the photosensitive element;
  c. a power source coupled to the capacitor network and the photosensitive element and adapted for charging the capacitor network; and
  d. means for measuring the duration of the discharge cycle of the capacitor network through the resistance developed by the photosensitive element in response to the intensity of the light emitted by the light source, wherein the light intensity is related to the duration of the discharge cycle;
 interposing said test devise into said light source and said light detection circuit; detecting the light intensity from said test device; and correlating said light intensity with the presence on amount of the analyte in said sample.

* * * * *